(12) United States Patent
Hale

(10) Patent No.: US 8,109,971 B2
(45) Date of Patent: Feb. 7, 2012

(54) ORTHOPEDIC FIXATION MECHANISM

(75) Inventor: Horace Winston Hale, Moerschwil (CH)

(73) Assignee: Horace Winston Hale, Moerschwil (CH)

( * ) Notice: Subject to any disclaimer, the term of this patent is extended or adjusted under 35 U.S.C. 154(b) by 609 days.

(21) Appl. No.: 11/926,865

(22) Filed: Oct. 29, 2007

(65) Prior Publication Data
US 2009/0157119 A1 Jun. 18, 2009

(51) Int. Cl.
*A61B 17/70* (2006.01)
(52) U.S. Cl. ............................. 606/247; 606/279
(58) Field of Classification Search ............... 606/86 A, 606/99, 60, 61, 246–249, 279, 300–321; 623/7.11–17.16
See application file for complete search history.

(56) References Cited

U.S. PATENT DOCUMENTS

| 6,679,917 | B2 | 1/2004 | Ek |
| 7,029,479 | B2 | 4/2006 | Tallarida et al. |
| 7,651,502 | B2 * | 1/2010 | Jackson ........................ 606/99 |
| 2005/0049705 | A1 | 3/2005 | Hale et al. |
| 2005/0060035 | A1 * | 3/2005 | Errico et al. ............... 623/17.15 |
| 2005/0071013 | A1 * | 3/2005 | Zubok et al. ............... 623/17.16 |
| 2005/0149030 | A1 | 7/2005 | Serhan et al. |
| 2005/0159746 | A1 * | 7/2005 | Grob et al. ...................... 606/61 |
| 2007/0055236 | A1 | 3/2007 | Hudgins et al. |
| 2007/0088358 | A1 | 4/2007 | Yuan et al. |
| 2007/0149983 | A1 | 6/2007 | Link |
| 2008/0125814 | A1 * | 5/2008 | Yuan et al. .................. 606/247 |

* cited by examiner

*Primary Examiner* — Eduardo C Robert
*Assistant Examiner* — Christina Negrelli
(74) *Attorney, Agent, or Firm* — Renner, Otto, Boisselle & Sklar LLP

(57) ABSTRACT

A fixation mechanism and method of fixation, such as the fixation of a facet resurfacing implant to an articular facet of a spinal vertebra. The fixation mechanism includes a securing mechanism having a socket configured to receive a knob of a biologic implant. The fixation mechanism further includes a locking mechanism for limiting expansion of the socket following engagement with the knob of the implant.

22 Claims, 11 Drawing Sheets

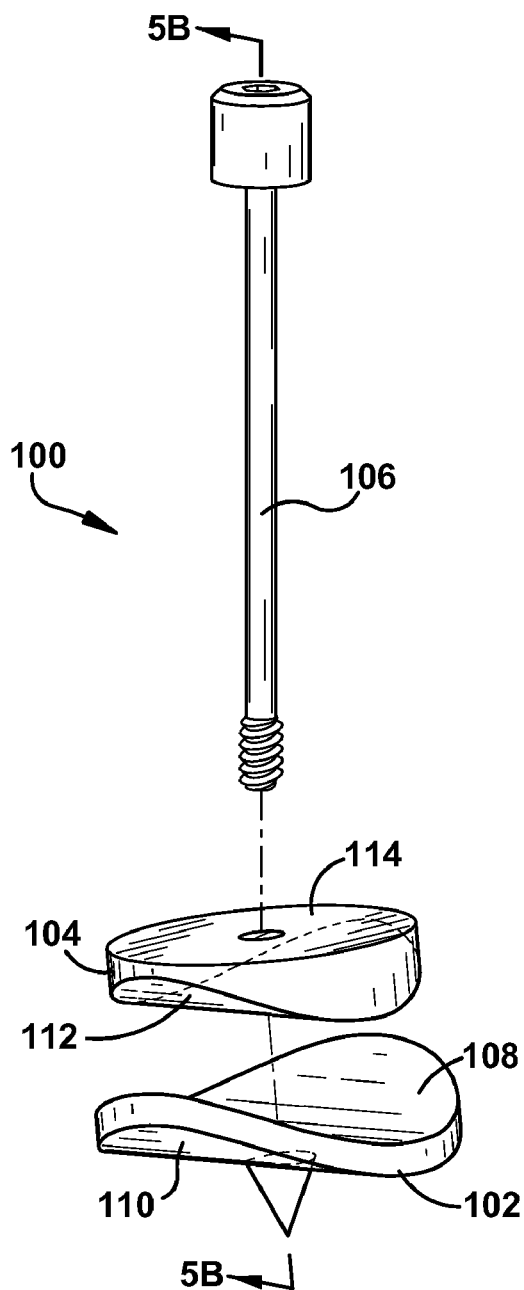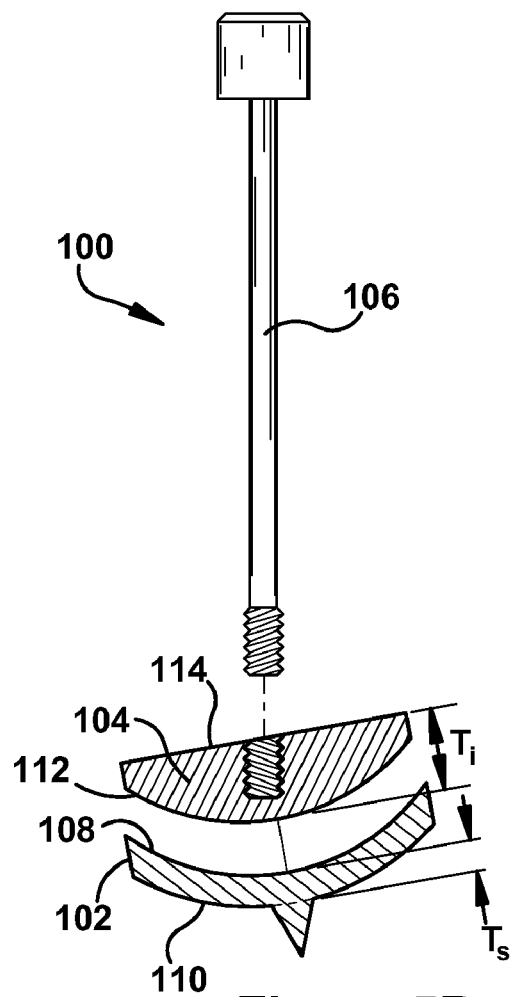
Figure 5A
Figure 5B

ORTHOPEDIC FIXATION MECHANISM

FIELD OF THE INVENTION

The present invention relates generally to prostheses for treating spinal pathologies, and more specifically to a system and method for treating articulating surfaces of facet joints.

BACKGROUND OF THE INVENTION

Back pain, such as in the "small of the back", or lumbosacral (L1-S1) region, is a common ailment. In many cases, the pain severely limits a person's functional ability and quality of life. A variety of spinal pathologies can lead to back pain.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort. With respect to vertebral articular surface degeneration, facet joints may show a reduced thickness of cartilage and may advance to entire disappearance thereof. Furthermore, surrounding the degenerated articular surfaces, there is bony formation able to give neurological compressions inside either the foramenae or spinal canal. These conditions induce lower back and nerve roots pain which affect a large part of the population.

The vertebral facet joints, for example, can be damaged by either traumatic injury or by various disease processes, such as osteoarthritis, ankylosing spondylolysis, and degenerative spondylolisthesis. The damage to the facet joints often results in pressure on nerves, also called a "pinched" nerve, or nerve impingement. The result is pain, malaligned anatomy, and a corresponding loss of mobility. Pressure on nerves can also occur without facet joint pathology, e.g., a herniated disc.

Degenerative spinal diseases can involve articular surfaces only, but may also have a more invasive pathology including traumatic, infectious, tumorous or dysmorphic (spondylolisthesis, for example) effecting the destruction of all or part of the articular process. The locking of vertebral motions by spinal arthrodesis or ligamentoplasty induces, beyond a spinal stiffness, an increased force on the joint facets of the adjacent vertebrae above and below the fusion, usually sustained by the considered intervertebral space resulting in an increase of degeneration of these joint facets.

One type of conventional treatment of facet joint pathology is spinal stabilization, also known as intervertebral stabilization. By applying intervertebral stabilization, one can prevent relative motion between the vertebrae. By preventing this movement, pain can be reduced. Stabilization can be accomplished by various methods. One method of stabilization is spinal fusion. Another method of stabilization is fixation of any number of vertebrae to stabilize and prevent movement of the vertebrae. Yet another type of conventional treatment is decompressive laminectomy. This procedure involves excision of the laminae to relieve compression of nerves. With regard to discal prostheses, a "space" is provided between two vertebral bodies while preserving some motion. This solves the aging intervertebral disc problem but does not function to reduce the force on posterior joint facets.

These traditional treatments are subject to a variety of limitations and varying success rates. For example, traditional treatments may result in limiting the patient's mobility or spontaneous fusion. There is a need in the art for a system and procedure capable of increasing the percentage of good results in disc replacement surgery. In addition, there is a need in the art for better results than are commonly achieved through trans-articular fusions. Further, there is a need in the art for a system and procedure that permits greater mobility in cases of spinal problems involving only the facet joints, and for obviating the need for spinal fusion associated with degenerative and congenital problems of the spine.

BRIEF SUMMARY OF THE INVENTION

Disclosed is a fixation mechanism for fixing an orthopedic implant comprising: a securing mechanism having a shaft and a socket, the socket being configured to engage a knob of the orthopedic implant; a sleeve at least partially surrounding the shaft, wherein the sleeve is configured to be positioned over at least a portion of the socket such that lateral expansion of the socket is limited by the sleeve; a locking element configured to engage the side of the securing mechanism opposite the socket to limit movement of the fixation mechanism with respect to a bone.

Also disclosed is a fixation mechanism wherein the socket and the knob of the orthopedic implant are snapably engageable.

Also disclosed is a fixation mechanism where the locking element and the sleeve are integrally formed.

Further disclosed is a fixation mechanism where the shaft comprises external threads and at least one of the sleeve or the locking element comprises internal threads.

Also disclosed is a facet implant comprising: an inferior implant configured for placement on an inferior articular facet of a vertebra, the inferior implant having a knob; and a fixation mechanism for securing the inferior implant to the inferior articular facet. The fixation mechanism comprises: a shaft, a socket configured to receive the knob of the inferior implant, and a locking mechanism for limiting expansion of the socket following receipt of the knob of the inferior implant.

Further disclosed is a facet implant where the fixation mechanism is capable of traversing a lamina connected to the inferior articular facet of the vertebra while engaging the knob of the inferior implant at or near the surface of an inferior articular facet of the vertebra.

Also disclosed is a facet implant comprising: a superior implant configured for placement on a superior articular facet, the superior implant having an articulating surface and a fixation surface; an inferior implant configured for placement on an inferior articulating facet, the inferior implant having an articulating surface, a fixation surface, and a knob extending from the fixation surface; and a fixation mechanism for securing the inferior implant to the inferior articular facet, the fixation mechanism comprising a socket configured to receive the knob of the inferior implant.

Further disclosed is a method for securing an implant having a knob to an inferior articular facet of a vertebra. The method comprises: creating a hole through the inferior articular facet; placing through the hole a fixation mechanism having a socket for receiving the knob of the implant; and engaging the implant and the fixation mechanism such that the knob of the implant is received by the socket.

Also disclosed is the use of at least one curette, at least one rasp or at least one high speed burr to prepare the inferior articular facet prior to engaging the implant and the fixation mechanism.

Further disclosed is the engagement of a locking element to fix the position of the fixation mechanism with respect to the vertebra.

Also disclosed is a method for providing artificial articulating surfaces for articular facets of vertebrae. The method comprises: placing an inferior implant having a knob on an articulating surface of an inferior articular facet; engaging the knob of the inferior implant with a socket of a fixation mechanism; and placing a superior implant on an articulating surface of a superior articular facet such that an articulating surface of the superior implant is capable of articulating with an articulating surface of the inferior implant.

Features that are described and/or illustrated with respect to one embodiment may be used in the same way or in a similar way in one or more other embodiments and/or in combination with or instead of the features of the other embodiments.

BRIEF DESCRIPTION OF THE SEVERAL VIEWS OF THE DRAWINGS

FIGS. 5A-5C illustrate a facet implant alone and in conjunction with a facet joint in a posterior perspective view;

DETAILED DESCRIPTION OF THE INVENTION

Figures 1, 2:
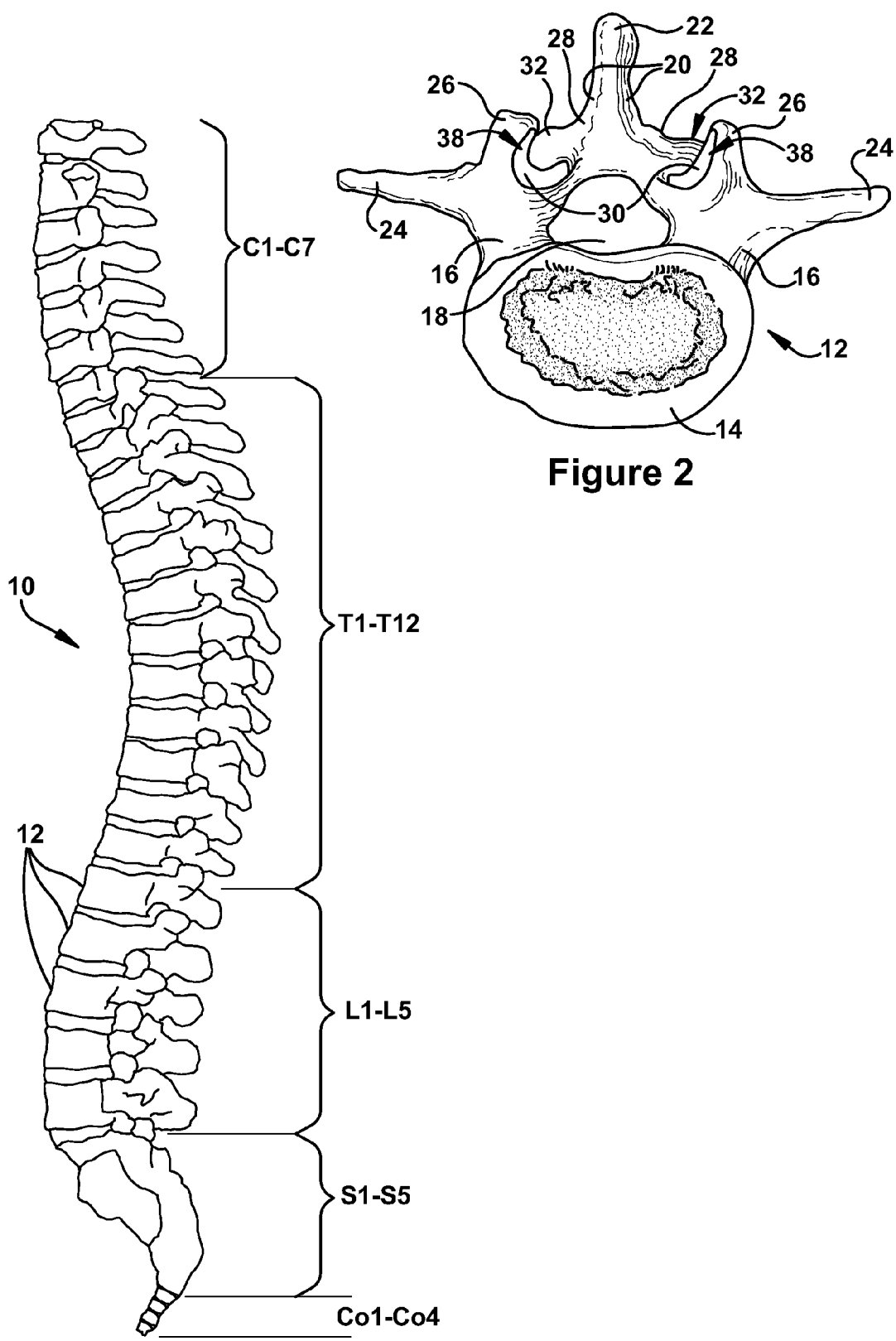
FIG. 1 is a lateral elevation view of a normal human spinal column.
FIG. 2 is a superior view of a normal human lumbar vertebra.

Referring initially to FIG. 1, the human spinal column 10 is illustrated. The spinal column 10 is comprised of a series of thirty-three stacked vertebrae divided into five regions. The cervical region includes seven vertebrae, known as C1-C7. The thoracic region includes twelve vertebrae, known as T1-T12. The lumbar region contains five vertebrae, known as L1-L5. The sacral region is comprised of five vertebrae, known as S1-S5. The coccygeal region contains four vertebrae 12, known as Co1-Co4.

Figure 3:
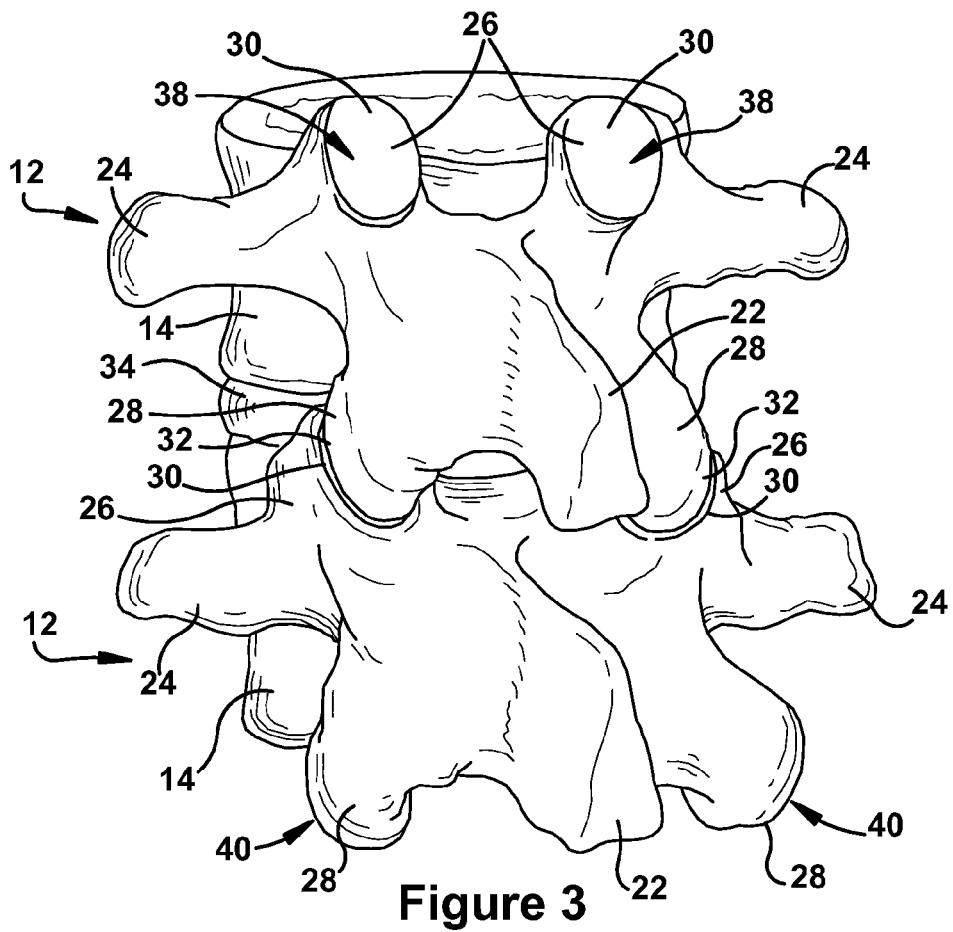
FIG. 3 is a posterior perspective view of a vertebral lumbar facet joint.

Turning now to FIGS. 2 and 3, normal human lumbar vertebrae 12 are illustrated. It will be understood by those skilled in the art that while the lumbar vertebrae 12 vary somewhat according to location, they share many features common to most vertebrae 12. Each vertebra 12 includes a vertebral body 14. Two short bones, the pedicles 16, extend backward from each side of the vertebral body 14 to form a vertebral arch 18. At the posterior end of each pedicle 16, the vertebral arch 18 flares out into broad plates of bone known as the laminae 20. The laminae 20 fuse with each other to form a spinous process 22. The spinuous process 22 provides muscle and ligament attachment.

The transition from the pedicles 16 to the laminae 20 is interrupted by a series of processes. Two transverse processes 24 thrust out laterally on each side from the junction of the pedicle 16 and the lamina 20. The transverse processes 24 serve as guides for the attachment of muscles to the vertebrae 12. Four articular processes, two superior 26 and two inferior 28, also rise from the junctions of the pedicles 16 and the laminae 20. The superior articular processes 26 are oval plates of bone rising upward on each side from the union of the pedicle 16 with the lamina 20. The inferior processes 28 are oval plates of bone jutting downward on each side. The superior and inferior articular processes 26 and 28, respectively, each have a natural bony structure known as a facet. The superior articular facet 30 faces upward, while the inferior articular facet 32 faces downward. The superior articular facet 30 and the inferior articular facet 32 have articulating surfaces 38 and 40, respectively.

Figure 4:
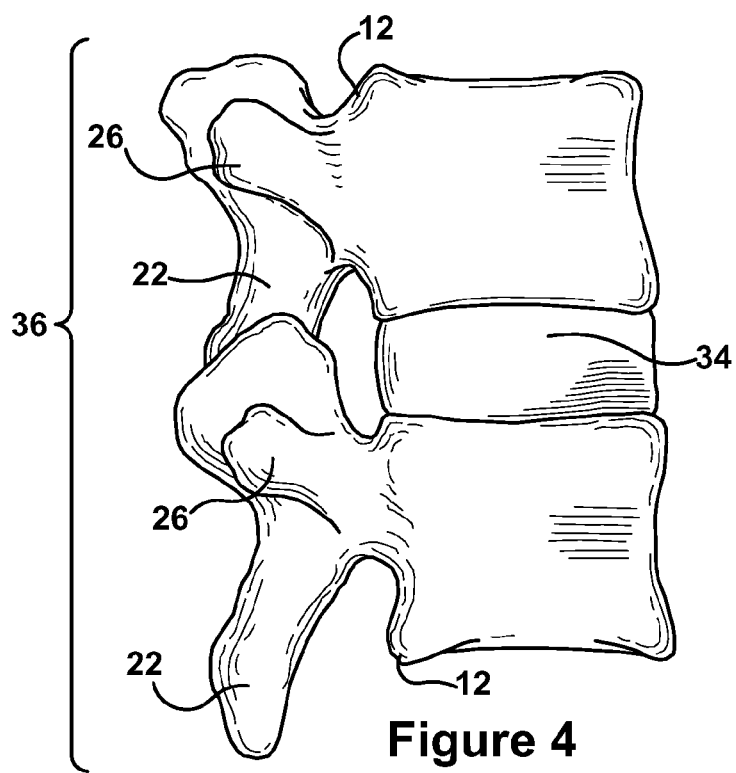
FIG. 4 is a lateral elevation view of a vertebral lumbar facet joint.

As shown in FIGS. 3 and 4, when adjacent vertebrae 12 are aligned, the superior articular facet 30 and inferior articular facet 32 interlock. Capped with a smooth articular cartilage, the interlocked vertebrae form a facet joint 36, also known as a zygapophysial joint. An intervertebral disc 34 between each pair of vertebrae 12 permits gliding movement between vertebrae 12. Thus, the structure and alignment of the vertebrae 12 permit a range of movement of the vertebrae 12 relative to each other.

The facet joint 36 is composed of a superior half and an inferior half. The superior half is formed by the vertebral level below the intervertebral disc 34, and the inferior half is formed by the vertebral level above the intervertebral disc 34. For example, in the L4-L5 facet joint, the superior portion of the joint is formed by bony structure on the L-5 vertebra (e.g., a superior articular surface and supporting bone on the L-5 vertebra), and the inferior portion of the joint is formed by bony structure on the L-4 vertebra (e.g., an inferior articular surface and supporting bone on the L-4 vertebra).

Figure 5C:
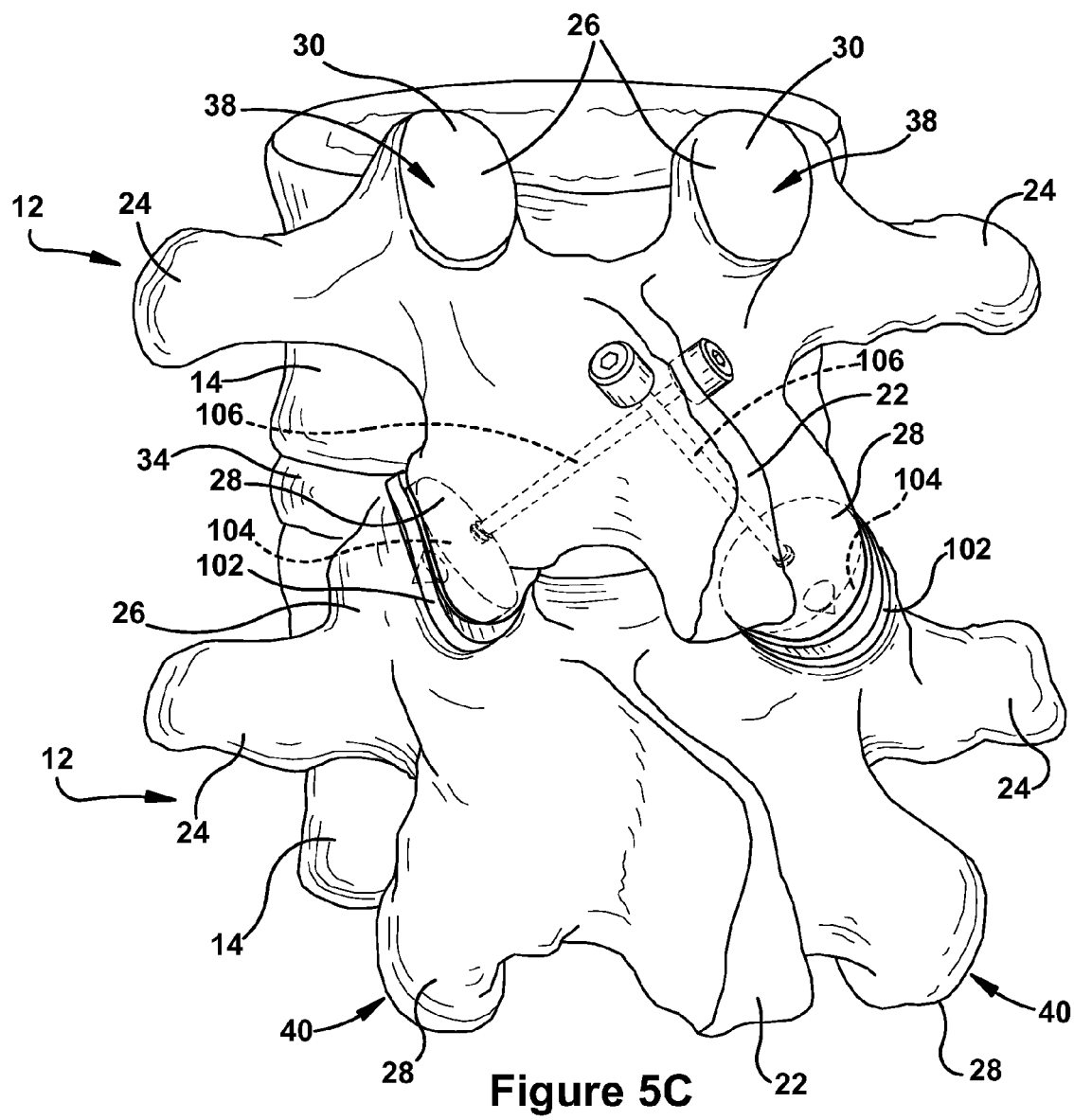

Turning now to FIGS. 5A and 5B, an exemplary facet implant according to the present invention is illustrated alone and in conjunction with a facet joint. The exemplary facet implant 100 generally has a superior implant 102 and an inferior implant 104. The superior implant 102 generally has an articulating surface 108 and a fixation surface 110. The inferior implant 104 generally has an articulating surface 112 and a fixation surface 114.

The superior implant 102 is configured for placement on the superior articular facet 30. The superior implant 102 may be fixed to the superior articulating surface 38 using cemented and/or cementless fixation techniques. In an exemplary embodiment, the superior implant 102 has an articulating surface 108 and a fixation surface 110 and is configured for placement on a specifically prepared superior articulating surface 38. The articulating surface 108 may be generally curved and may be configured to interact with an articulating surface 112 of the inferior implant 104.

The superior implant 102 may have a surface fixation mechanism for fixing the superior implant 102, such as by fixing the fixation surface 110, to the superior articulating surface 38. The surface fixation mechanism may be any fixation mechanism known in the art, such as: one or more pegs, one or more pips, ridges or grooves, one or more screws. In an exemplary embodiment, the surface fixation mechanism includes a plurality of ridges, grouped in regions such that the ridges in different regions are oriented in different directions. For example, the surface fixation mechanism may include four regions on the fixation surface 110 where each of the four regions has ridges oriented in a different direction. The various orientations of the ridges prevent the superior implant 102 from moving in different directions with respect to the superior articulating surface 38.

The fixation surface 110 of the superior implant 102 may also have a porous coating; a porous onlay material; a biologic coating; a surface treatment, such as to facilitate bone ingrowth or cement fixation; and combinations thereof. For example, the fixation surface 110 may have a porous surface that is beaded, threaded, textured, etc. Further, the fixation surface 110 may have a hydroxyapatite coating or may be plasma-sprayed. In addition to the examples listed, any known method of improving fixation of biologic implants may be used to improve the interaction of the fixation surface 110 and the superior articular facet 30.

In one exemplary embodiment, the fixation surface 110 of the superior implant 102 is configured to interact only with the superior articulating surface 38 and does not interact directly with any other aspect of the superior articular facet 30, the superior articular process 26, or even the facet joint 36. The fixation surface 110 of the superior implant 102 may be generally curved for improved interaction with the superior articulating surface 38.

The articulating surface 108 in one exemplary embodiment is generally configured to articulate or interact with the articulating surface 112 of the inferior implant 104. Accordingly, the articulating surface 108 of the superior implant 102 may be generally curved. The superior implant 102 articulating surface 108 may be configured such that it acts as a "female" surface wherein it is concave or configured to accept a "male" articulating surface 112 of an inferior implant 104. Conversely, the superior implant 102 articulating surface 108 may also be configured such that it acts as a "male" surface wherein it is convex or configured to be accepted by "female" articulating surface 112 of an inferior implant 104.

The superior implant 102 may be composed of any material commonly used in the art for articulating medical implants. Such materials include, but are not limited to, cobalt-chromium alloys, ceramics (alumina ceramic, zirconia ceramic, yttria zirconia ceramic, etc.), titanium, ultra high molecular weight polyethylene (UHMWPE), pyrolytic carbon, titanium/aluminum/vanadium (Ti/Al/V) alloys, Tantalum, carbon composite materials and combinations thereof. For example, the superior implant 102 may be generally composed of titanium, but have a UHMWPE articulating surface 108. Some materials are more appropriate for articulating surfaces and some more appropriate for fixation surfaces, but any materials known in the art for use with articulating and fixation surfaces may be used in the present invention. Such materials are commonly used in joint arthroplasty and the like.

The superior implant 102 may be from about 2 mm thick to about 15 mm thick. In an exemplary embodiment, the thickness (Ts) of the superior implant 102 ranges from about 6 mm to about 10 mm. In another exemplary embodiment, the thickness (Ts) of the superior implant 102 ranges from about 3 mm to about 5 mm.

The inferior implant 104 is configured for placement on inferior articular facet 32. The inferior implant 104 may be fixed to the inferior articulating surface 40 using cemented and/or cementless fixation techniques. In an exemplary embodiment, the inferior implant 104 has an articulating surface 112 and a fixation surface 114 and is configured for placement on a specifically prepared inferior articulating surface 40. The articulating surface 112 may be generally convex and may be configured to interact with an articulating surface 108 of the superior implant 102.

The inferior implant 104 may have a surface fixation mechanism for fixing the inferior implant 104, such as by fixing the fixation surface 114, to the inferior articulating surface 40. The surface fixation mechanism may be any fixation mechanism known in the art, such as: one or more pegs, ridges or grooves, one or more screws. In an exemplary embodiment, the surface fixation mechanism includes a plurality of ridges, grouped in regions such that the ridges in different regions are oriented in different directions. For example, the surface fixation mechanism may include four regions on the fixation surface 114 where each of the four regions has ridges oriented in a different direction. The various orientations of the ridges prevent the inferior implant 104 from moving in different directions with respect to the inferior articulating surface 40.

The fixation surface 114 of the inferior implant 104 may also have a porous coating; a porous onlay material; a biologic coating; a surface treatment, such as to facilitate bone ingrowth or cement fixation; and combinations thereof. For example, the fixation surface 114 may have a porous surface that is beaded, threaded, textured, etc. Further, the fixation surface 114 may have a hydroxyapatite coating or may be plasma-sprayed. In addition to the examples listed, any known method of improving fixation of biologic implants may be used to improve the interaction of the fixation surface 114 and the inferior articular facet 32.

In one exemplary embodiment, the fixation surface 114 of the inferior implant 104 is configured to interact only with the inferior articulating surface 40 and does not interact directly with any other aspect of the inferior articular facet 32, the inferior articular process 28, or even the facet joint 36. The fixation surface 114 of the inferior implant 104 may be generally flat or generally curved for improved interaction with the inferior articulating surface 40.

In another exemplary embodiment, the inferior implant 104 is configured to interact with or attach to a translaminar fixation mechanism 106. For example, the inferior implant 104 may include a threaded hole either extending from or bored into the fixation surface 114 of the inferior implant 104. The manner in which the inferior implant 104 and the translaminar fixation mechanism 106 interact may vary with different anatomies. For example, it may be preferable to offset the translaminar fixation mechanism 106 from the inferior implant 104 such that when the translaminar fixation mechanism 106 and inferior implant 104 interact, the translaminar fixation mechanism 106 is not perpendicular to the inferior implant 104. The translaminar fixation mechanism 106 may range from about 0 degrees offset from perpendicular to about 20 degrees offset from perpendicular. In one exemplary embodiment, the translaminar fixation mechanism 106 ranges from about 5 degrees offset from perpendicular to about 15 degrees offset from perpendicular. In another exemplary embodiment, the translaminar fixation mechanism 106 is about 10 degrees offset from perpendicular.

The articulating surface 112 of the inferior implant 104 in one exemplary embodiment is generally configured to articulate or interact with the articulating surface 108 of the superior implant 102. Accordingly, the articulating surface 112 of the inferior implant 104 may be generally convex. The inferior implant 104 articulating surface 112 may be configured such that it acts as a "male" surface wherein it is convex or configured to be accepted by a "female" articulating surface 108 of a superior implant 102. Conversely, the inferior implant 104 articulating surface 112 may also be configured such that it acts as a "female" surface wherein it is configured to accept a "male" articulating surface 108 of a superior implant 102.

The inferior implant 104 may be composed of any material commonly used in the art for articulating medical implants. Such materials include, but are not limited to, cobalt-chromium alloys, ceramics (alumina ceramic, zirconia ceramic, yttria zirconia ceramic, etc.), titanium, ultra high molecular weight polyethylene (UHMWPE), pyrolytic carbon, titanium/aluminum/vanadium (Ti/Al/V) alloys, and combinations thereof. For example, the inferior implant 104 may be generally composed of a ceramic material or a cobalt-chromium alloy. Some materials are more appropriate for articulating surfaces and some more appropriate for fixation surfaces, but any materials known in the art for use with articulating and fixation surfaces may be used in the present invention. Such materials are commonly used in joint arthroplasty and the like.

The inferior implant 104 may be from about 2 mm thick to about 15 mm thick. In an exemplary embodiment, the thickness (Ti) of the inferior implant 104 ranges from about 6 mm to about 12 mm. In another exemplary embodiment, the thickness (Ti) of the inferior implant 104 ranges from about 3 mm to about 5 mm.

One exemplary embodiment of the present invention includes a translaminar fixation mechanism 106 configured to interact with the inferior implant 104. The translaminar fixation mechanism 106 secures the inferior implant 104 to the inferior articular facet 32. The translaminar fixation mechanism 106 may be any fixation mechanism known in the art, such as a translaminar screw. The translaminar fixation mechanism 106 may be made from any material known in art for medical fixation devices. For example, the translaminar fixation mechanism 106 may be made from titanium, titanium/aluminum/vanadium (Ti/Al/V) alloys, Tantalum, CrCo, ceramic, carbon or carbon composite materials.

Figure 6:
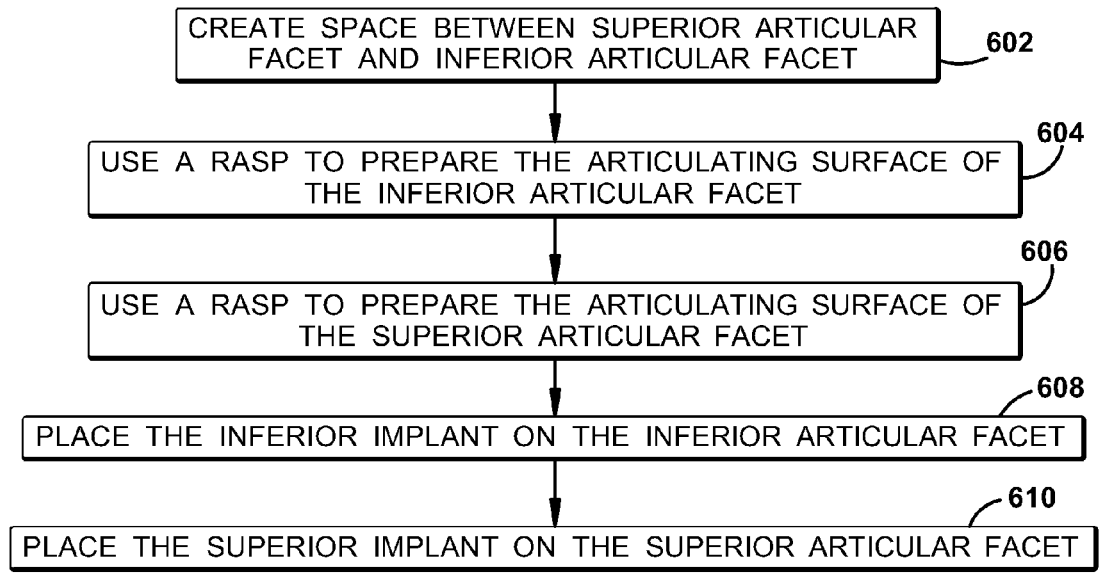
FIG. 6 is a flow chart generally illustrating a method for providing articulating surfaces for facet joint articular facets.

Turning next to FIG. 6, there is provided a flow diagram generally illustrating a method for providing articulating surfaces for facet joint articular facets. The overall flow begins at process block 602 wherein a space is created between the superior articular facet 30 and the inferior articular facet 32. It will be understood by those skilled in the art that prior to creating the space, it may be preferable or even necessary to expose the facet joint 36 at an affected level and remove the capsule. The affected level may be exposed through use of any appropriate procedure, such as a modified "Wiltse" approach. The creation of the space at process block 602 may be accomplished by using a curette or similar device and by removing the cartilaginous surfaces of the facet joint 36. In one exemplary embodiment, the created space is sufficient for using a rasp on an articulating surface of an articular facet. The space created between the superior articular facet 30 and the inferior articular facet 32 may range, for example, from about 2 mm to about 5 mm. In one exemplary embodiment, the space ranges from about 3 mm to about 4 mm.

Flow progresses to process block 604 wherein a rasp is used to prepare the articulating surface 40 of the inferior articular facet 32 for an inferior implant 104. Progression then continues to process block 606 wherein a rasp is used to prepare the articulating surface 38 of the superior articular facet 30 for a superior implant 102.

Figure 8:
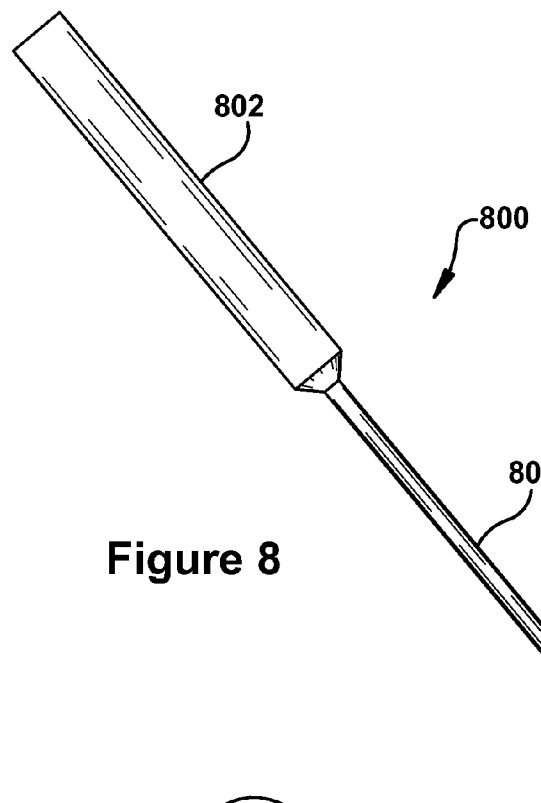
FIGS. 8-10 are illustrations of different types of rasps.
Figure 9:
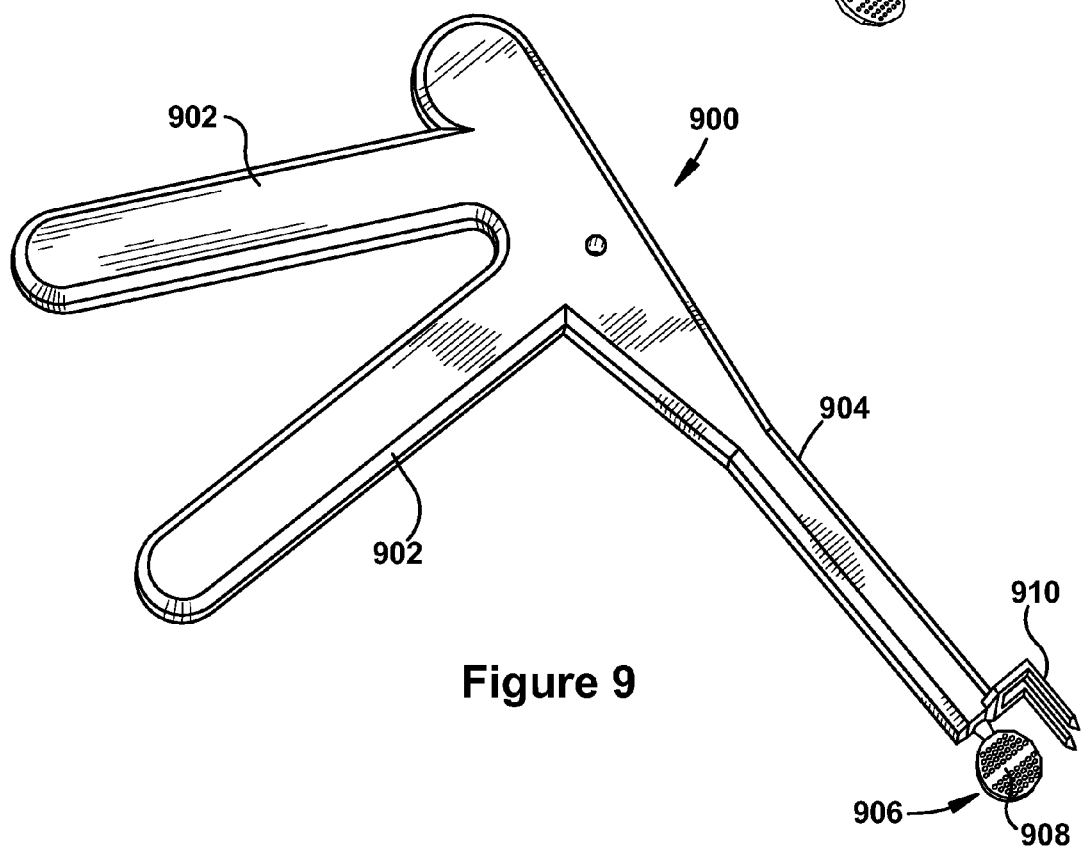
Figure 10:
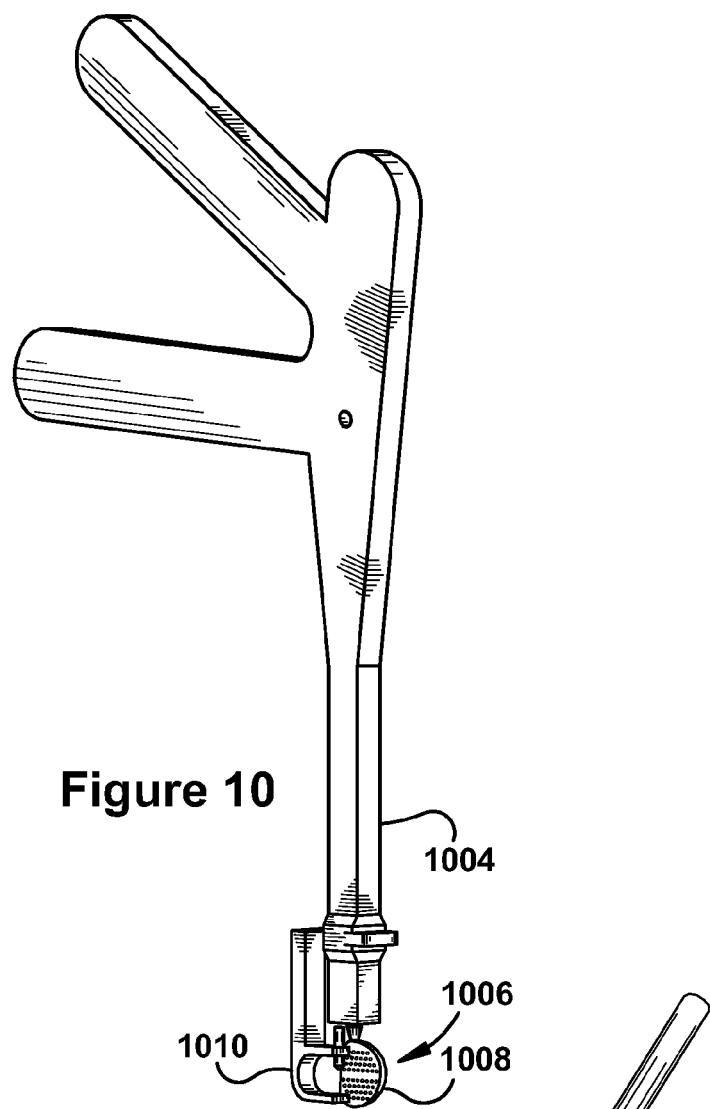

Each of the rasps of process blocks 604 and 606 may be either a single shaft rasp or a double action rasp, such as those illustrated in FIGS. 8-10 and described in detail herein. The process of preparing the articulating surfaces 38 and 40 of the articular facets 28 and 30 may involve using multiple rasps of increasing thickness while widening the space created in process block 602. For example, a 2 mm rasp may initially be used, then a 4 mm rasp, then a 6 mm rasp, then an 8 mm rasp, etc., until a desired result is achieved. In addition, the rasps of process blocks 604 and 606 may be the same rasp. Further, a single rasp can be used to prepare the articulating surfaces 38 and 40 concurrently. The articulating surfaces 38 and 40 may be prepared such that a bleeding bone bed is created to facilitate bone ingrowth for the superior implant 102 and inferior implant 104.

Figure 7:
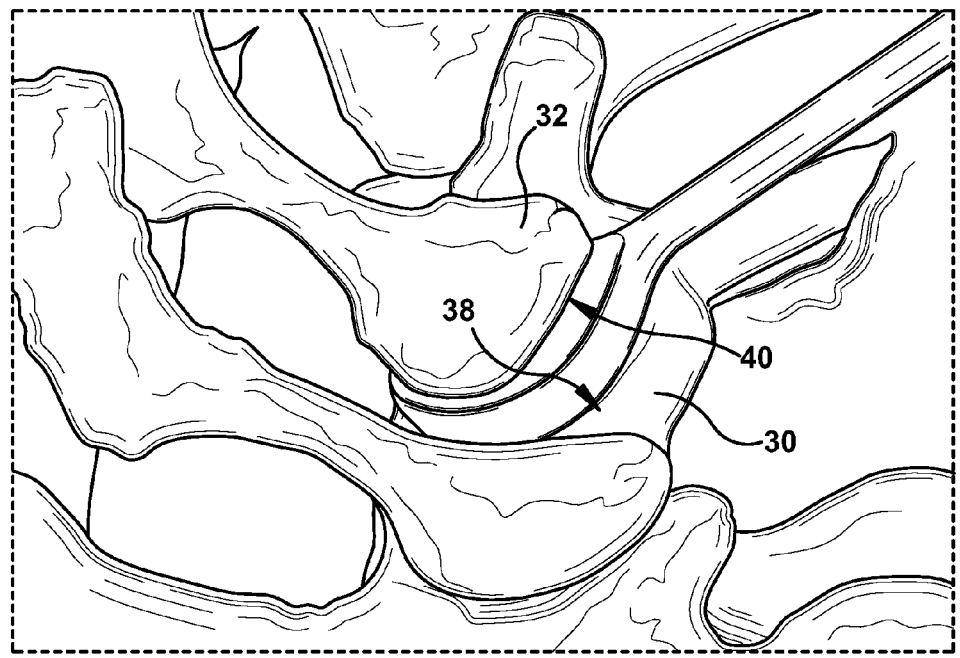
FIG. 7 is an illustration of a rasp being used to prepare an articulating surface.

As shown in FIG. 7, when the single handed rasp is used to prepare articulating surface 38 and/or articulating surface 40, the working end of the tool may be positioned inside the space created in process block 602. The rasp may then be moved from an anterior to a posterior position inside the facet joint 36 in order to effect a clean and uniform resection of the created space in the shape and dimension of both implants. In other words, the articulating surface 38 is prepared such that its shape and dimension resembles the superior implant 102 and the articulating surface 40 is prepared such that its shape and dimension resembles the inferior implant 104. The anterior/posterior movement of the rasp may be continued until the rasp is too small for the space created. The rasp may be too small when the space created is so wide that the rasp cannot prepare both the articulating surfaces 38 and 40 concurrently. A larger (thicker) rasp may then be used. Increasingly larger rasps may be used until the created space is increased such that it ranges from about 4 mm to about 15 mm. In one exemplary embodiment, the rasps are designed to cut only when moving in a posterior direction to help prevent injury during the resurfacing process.

When a double action rasp is used, the working end of the rasp is positioned inside the created space and then the fixation appendages are secured to the lamina or to a cephalad position of the superior facet 26. The rasp is then moved in a cephalad/caudad direction by alternately squeezing and releasing the handles. Like the single handed rasp, double action rasp creates a clean and uniform resection of the created space in the shape and dimension of both implants. The alternately squeezing and releasing of the handles may be continued until the rasp is too small for the space created. The rasp may be too small when the space created is so wide that the rasp cannot prepare both the articulating surfaces 38 and 40 concurrently. A larger (thicker) rasp may then be used. Increasingly larger rasps may be used until the created space is increased such that it ranges from about 4 mm to about 15 mm. In one exemplary embodiment, the rasps are designed to cut only when moving in a caudad direction to help prevent injury during the resurfacing process.

In one embodiment, the steps of process blocks 602, 604 and 606 are repeated on the contralateral side of facet joint 36 prior to performing the steps of process block 608.

Progression then flows to process block 608 wherein the inferior implant 104 is placed on the prepared/resurfaced articulating surface 40 of the inferior articular facet 32. In one exemplary embodiment, the inferior implant 104 is placed such that it interacts with the articulating surface 40 of the inferior articular facet 32, but not with other aspects of the inferior articular facet 32.

In one exemplary embodiment, a translaminar fixation mechanism 106 is used to secure the inferior implant 104 to the inferior articular facet 32. In this embodiment, the above method would also include using the translaminar fixation mechanism 106 to secure the inferior implant 104 to the inferior articular facet 32. This exemplary embodiment preferably includes placing the translaminar fixation mechanism 106 prior to placing the inferior implant 104 described in process block 608.

Figure 11:
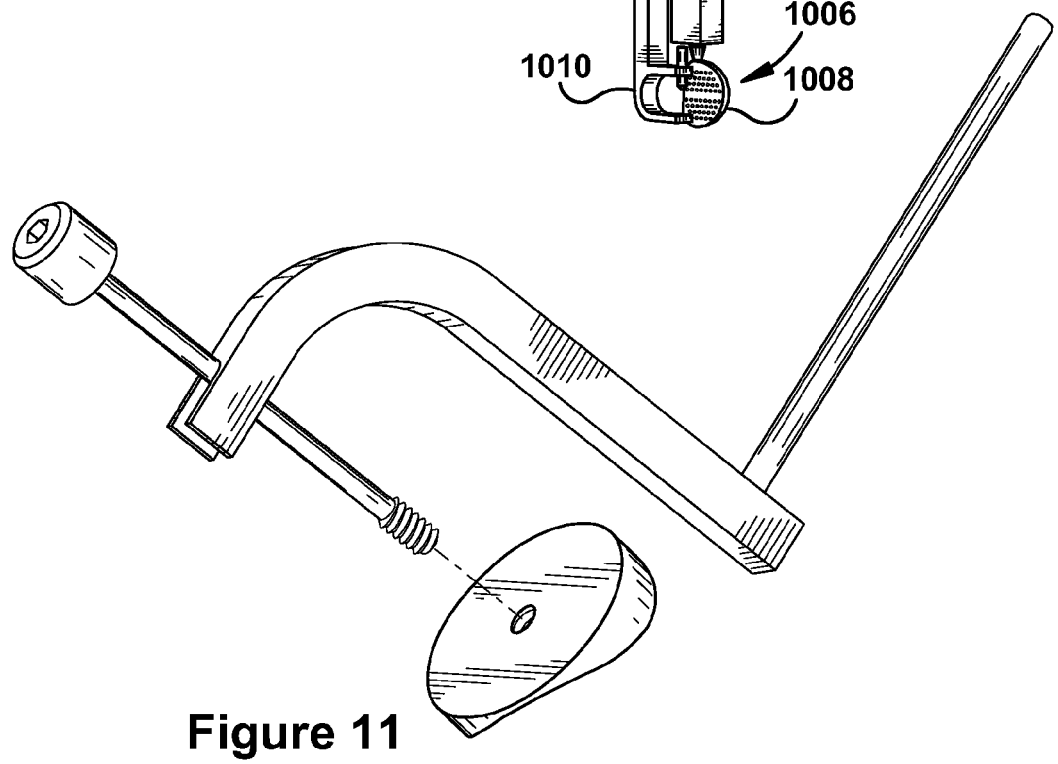
FIG. 11 is an illustration of an aiming device for use in positioning a translaminar fixation mechanism.

To facilitate placement of the translaminar fixation mechanism 106, an aiming device such as the one illustrated in FIG. 11 may be used. The aiming device can be used to position a drill for creating a translaminar hole for the translaminar fixation mechanism 106. A drill can then be used to create the hole, which may have a diameter of about 2 mm, depending on the diameter of the translaminar fixation mechanism 106. Once the hole is drilled, the translaminar fixation mechanism 106 can be introduced into the hole and then used to secure the inferior implant 104 to the inferior articular facet 32.

In one embodiment, the steps of process blocks 608, including any steps associated with the drilling or placement of the translaminar fixation mechanism 106, are repeated on the contralateral side of facet joint 36 prior to performing the steps of process block 610.

Progression then continues to process block 610 wherein the superior implant 102 is placed on the prepared/resurfaced articulating surface 38 of the superior articular facet 30. In one exemplary embodiment, the superior implant 102 is placed such that it interacts with the articulating surface 38 of the superior articular facet 30, but not with other aspects of the superior articular facet 30.

In one embodiment, the steps of process blocks 602, 604, 606, 608 and 610 are then repeated on the contralateral side.

Turning now to FIG. 8, a single handed rasp is illustrated. The rasp 800 includes a handle 802 and a shaft 804 connecting the handle 802 to the working end of the rasp 800. Attached to the shaft 804 at the working end of the rasp 800 is a head 806. The head 806 has at least one cutting surface 808. In one exemplary embodiment, the cutting surface 808 is configured to cut when the cutting surface 808 is moved in a first direction (e.g. when the rasp is moved from the anterior to the posterior direction of the facet joint) but not when the cutting surface 808 is moved in a direction opposite to the first direction (e.g. when the rasp is moved from the posterior to the anterior direction of the facet joint).

Turning now to FIG. 9, a double action rasp is illustrated. The rasp 900 includes two handles 902 and a shaft 904 connecting the handles 902 to the working end of the rasp 900. Attached to the shaft 904 at the working end of the rasp 900 are a head 906 and at least one fixation appendage 910. The head 906 has at least one cutting surface 908. In one exemplary embodiment, the cutting surface 908 is configured to cut when the cutting surface 908 is moved in a first direction (e.g. when the rasp is moved in a cephalad direction of the facet joint) but not when the cutting surface 908 is moved in a direction opposite to the first direction (e.g. when the rasp is moved in a caudad direction of the facet joint). In addition, the fixation appendages 910 may be configured for interaction with the lamina 20 or with a cephalad position of the superior facet 26. In one exemplary embodiment of a double action rasp 900, squeezing the handles 902 of the rasp 900 causes the head 906 to move in a cephalad position and releasing the handles 902 causes the head 906 to move in a caudad direction.

Turning now to FIG. 10, another double action rasp is illustrated. Attached to the shaft 1004 at the working end of the rasp 1000 are a head 1006 and a fixation appendage 1010. The fixation appendage 1010 may be rigid or capable of pivoting to accommodate various working angles. The head 1006 has at least one cutting surface 1008. In one exemplary embodiment, the cutting surface 1008 is configured to cut when the cutting surface 1008 is moved in a first direction but not when the cutting surface 1008 is moved in a direction opposite to the first direction. In one exemplary embodiment, the rasp is a double action rasp like the rasp 900 where squeezing the handles of the rasp causes the head 1006 to move in a first direction and releasing the handles causes the head 1006 to move in a second direction.

The rasps 800, 900 and 1000 of FIGS. 8-10 are configured to prepare the articulating surfaces of a facet joint. In an exemplary embodiment, the rasps 800, 900 and 1000 are configured to prepare articulating surfaces 38 and 40 of the articular facets 28 and 30 such that the shape and dimension of the prepared articulating surfaces resembles the shape and dimension of the superior implant 102 and inferior implant 104. For example, if the superior implant 102 and/or inferior implant 104 are curved, the head 806, 906 and 1006 may be generally curved to properly prepare the surface for the implant.

In addition, the rasps 800, 900 and 1000 may be made from any appropriate material commonly used for medical tools. In one exemplary embodiment, at least part of the rasps 800, 900 and 1000 are made from titanium, although the rasps could also be made from any material known in the art.

Figures 12A, 12B:
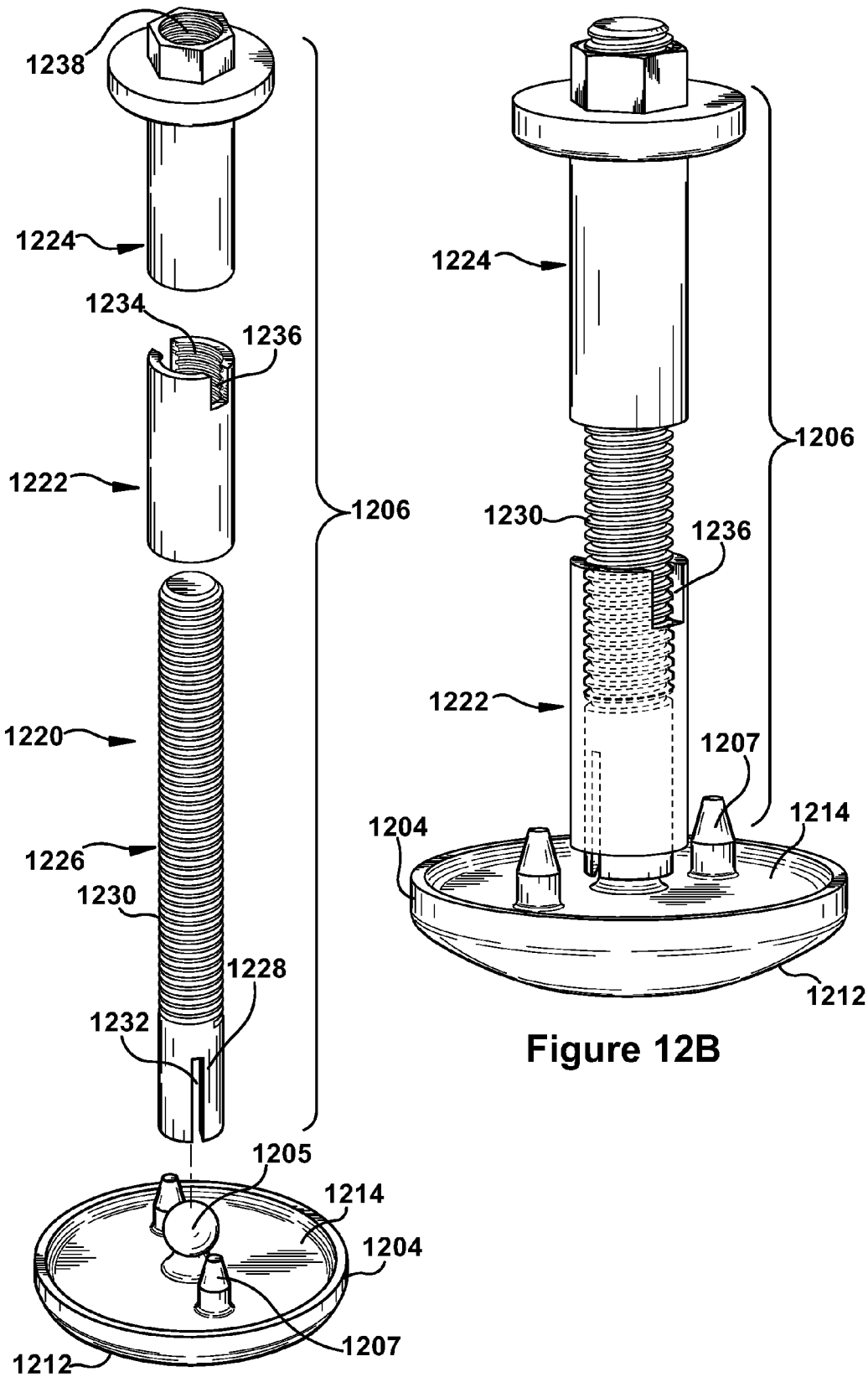
FIG. 12A is an exploded perspective view of an inferior articular facet implant with an embodiment of a novel fixation mechanism.
FIG. 12B is a perspective view of an inferior articular facet implant and an embodiment of a novel fixation mechanism in a locked position.
Figures 13A, 13B:
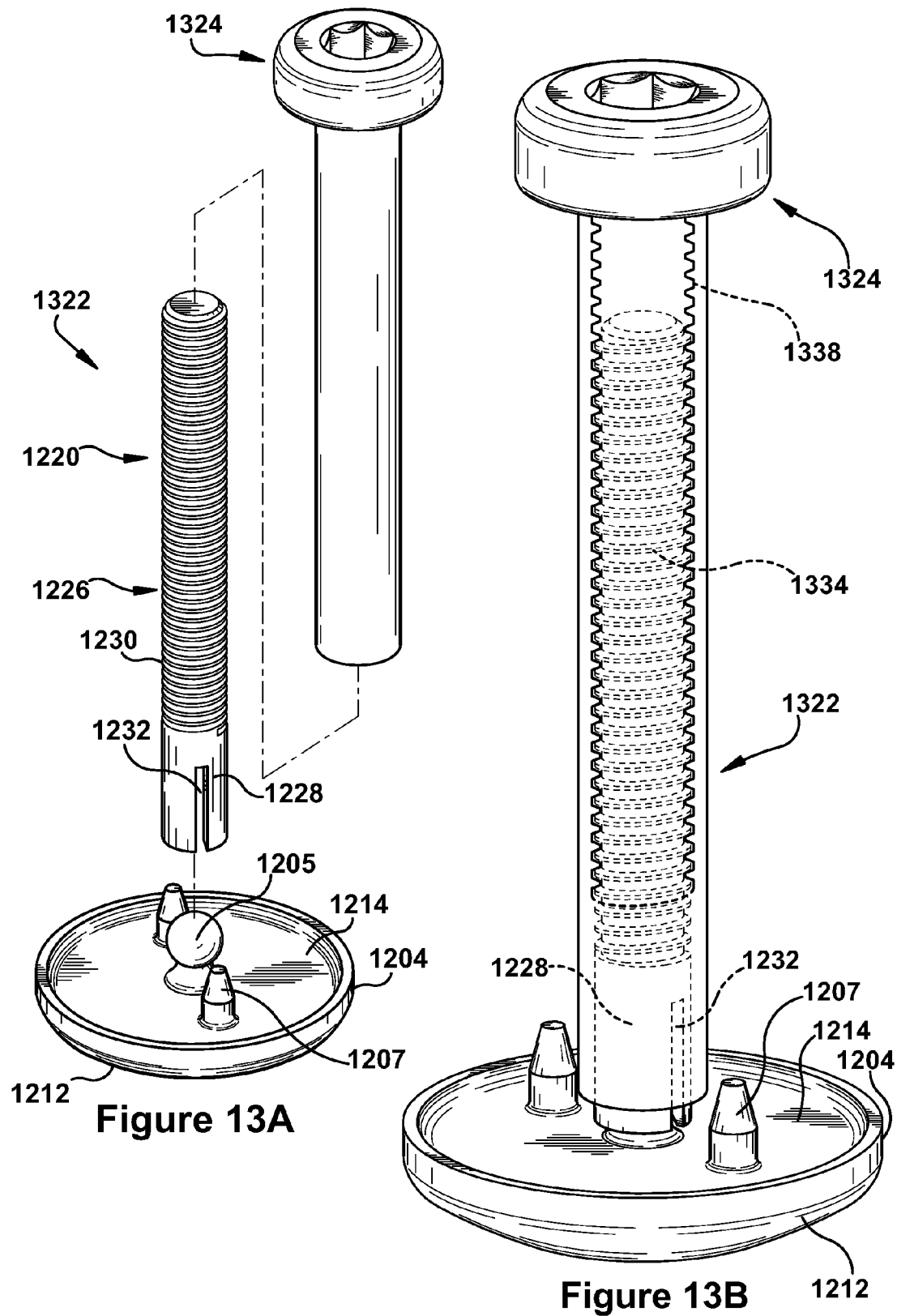
FIG. 13A is an exploded perspective view of an inferior articular facet implant with another embodiment of a novel fixation mechanism.
FIG. 13B is a perspective view of an inferior articular facet implant and another embodiment of a novel fixation mechanism in a locked position.

Turning next to FIGS. 12A-B and 13A-B, FIGS. 12A and 13A are exploded perspective views of an inferior articular facet implant in conjunction with embodiments of novel fixation mechanisms and FIGS. 12B and 13B are perspective views of an inferior articular facet implant and the fixation mechanisms of FIGS. 12A and 13A in locked positions. It should be understood that the fixation mechanisms and inferior implants of FIGS. 12A-B and 13A-B may be used in conjunction with the superior implant 102. In this manner, the fixation mechanism may be translaminar fixation mechanism used in lieu of translaminar fixation mechanism 106. As such, the fixation mechanisms of FIGS. 12A-B and 13A-B may be capable of traversing a lamina connected to the inferior articular facet of a vertebra while engaging a knob of an inferior implant at or near the surface of an inferior articular facet of the vertebra. In addition, while the exemplary embodiments describe the fixation mechanism as it may be used to fix an articular resurfacing implant, it will be understood by those skilled in the art that the fixation mechanisms 1206 and 1306 may be used with other types of biologic implants and are not limited to use with the spine.

The inferior implant 1204 generally has an articulating surface 1212 and a fixation surface 1214. Like the inferior implant 104, the inferior implant 1204 may be configured for placement on an inferior articular facet, such as the inferior articular facet 32 and may be fixed using cemented and/or cementless fixation techniques.

In addition, the inferior implant 1204 is preferably convex and configured to interact with an articulating surface of a superior implant, such as the articulating surface 108 of the superior implant 102. Preferably, the inferior implant 1204 articulating surface 1212 may be configured such that it acts as a "male" surface wherein it is convex or configured to be accepted by a "female" articulating surface 108 of a superior implant 102. Conversely, however, the inferior implant 1204 articulating surface 1212 may also be configured such that it acts as a "female" surface wherein it is configured to accept a "male" articulating surface 108 of a superior implant 102.

The inferior implant 1204 also has a fixation surface 1214 which is preferably configured to interact with an inferior articulating surface of a vertebra, such as the inferior articulating surface 40 of a vertebra 12. The fixation surface 1214 of the inferior implant 1204 may be generally flat or generally curved for improved interaction with an inferior articulating surface of a vertebra.

The inferior implant 1204 may have a surface fixation mechanism for facilitating fixation of the inferior implant 1204 to the inferior articulating surface 40. The surface fixation mechanism may be any fixation mechanism known in the art, such as: one or more spikes, pegs, ridges or grooves, one or more screws. In an exemplary embodiment of FIGS. 12A-B, the surface fixation mechanism includes spikes 1207. In addition, the surface fixation mechanism may include four regions on the fixation surface 1214 where each of the four regions has ridges oriented in a different direction. The various orientations of the ridges prevent the inferior implant 1204 from moving in different directions with respect to the inferior articulating surface.

The fixation surface 1214 of the inferior implant 104 may also have a porous coating; a porous onlay material; a biologic coating; a surface treatment, such as to facilitate bone ingrowth or cement fixation; or combinations thereof. For example, the fixation surface 1214 may have a porous surface that is beaded, threaded, textured, etc. Further, the fixation surface 1214 may have a hydroxyapatite coating or may be plasma-sprayed. In addition to the examples listed, any known method of improving fixation of biologic implants may be used to improve the interaction of the fixation surface 1214 and the inferior articular facet.

Extending from the fixation surface 1214 is a knob 1205. As used herein, a knob is any knob-like object and is not limited to the specific type of spherical knob disclosed in FIGS. 12A-B and 13A-B. The type of knob used according to the present invention may vary, just as, for example, door knobs vary in design. The knob 1205 is preferably configured to interact with a fixation mechanism, such as fixation mechanism 1206.

The inferior implant 1204 may be composed of any material commonly used in the art for articulating medical implants. Such materials include, but are not limited to, cobalt-chromium alloys, ceramics (alumina ceramic, zirconia ceramic, yttria zirconia ceramic, etc.), titanium, ultra high molecular weight polyethylene (UHMWPE), pyrolytic carbon, titanium/aluminum/vanadium (Ti/Al/V) alloys, or combinations thereof. For example, the inferior implant 1204 may be generally composed of a ceramic material or a cobalt-chromium alloy. Some materials are more appropriate for articulating surfaces and some more appropriate for fixation surfaces, but any materials known in the art for use with articulating and fixation surfaces can be used in the present invention. Such materials are commonly used in joint arthroplasty and the like.

The inferior implant 1204 may be from about 2 mm thick to about 15 mm thick. In an exemplary embodiment, the thickness of the inferior implant 1204 preferably ranges from about 6 mm to about 12 mm.

To secure the inferior implant 1204 to an inferior articular facet, the fixation mechanism 1206 includes a securing mechanism 1220 having a shaft 1226 and a socket 1228, as well as a locking mechanism having a sleeve 1222 and a locking element 1224. The shaft 1226 may have threads 1230 for interacting with other parts of the fixation mechanism 1206. The socket 1228 is generally configured to engage the knob 1205 of the inferior implant 1204. In one embodiment, the socket 1228 and knob 1205 are snapably engageable. In addition, the socket 1228 may include slots, such as slots 1232 to facilitate expansion, for example, during engagement and disengagement with the knob 1205.

The fixation mechanism 1206 also has a sleeve 1222 at least partially surrounding the shaft 1226 and moveable with respect to the shaft 1226. Preferably, the sleeve 1222 is configured to be positioned over at least a portion of the socket 1228 such that the lateral expansion of the socket 1228 is limited by the sleeve 1222. In use, the sleeve 1222 is preferably positioned over at least a portion the socket 1228 following engagement of the socket 1228 and knob 1205 to prevent the knob 1205 and the socket 1228 from disengaging.

During engagement, the inferior implant 1204 and fixation mechanism may range from about 0 degrees offset from perpendicular to about 30 degrees offset from perpendicular. In one exemplary embodiment, the inferior implant 1204 and the fixation mechanism 1206 ranges from about 5 degrees offset from perpendicular to about 15 degrees offset from perpendicular. It will be understood by those skilled in the art the knob 1205 and socket 1228 engagement permits a wide range of engagement angles and that the range of engagement angles can be altered by varying the distance from the bottom of the knob 1205 to the fixation surface 1214 of the inferior implant 1204.

The sleeve 1222 may have access slots, such as slots 1236, to facilitate engagement with a driver or other tool, which may be used to position the sleeve 1222 over at least a portion of the socket 1228. In one embodiment, the sleeve 1222 has threads 1234 on at least part of the internal surface of the sleeve 1222 for engagement with the threads 1230 of the shaft 1226. For example, the sleeve 1222 may be only partially threaded such that the area to be positioned over at least a portion of the socket 1228 is not internally threaded.

The fixation mechanism 1206 further includes a locking element 1224 that may be configured to engage the side of the securing mechanism 1220 opposite the socket 1228 to limit movement of the fixation mechanism 1206 with respect to a bone. Preferably, the locking element 1224 is also a lagging element that lags the inferior implant 1204 as the locking element 1224 is engaged. The locking element 1224 may have internal threads 1238 for engaging the external threads 1230 of the shaft 1226. In the embodiment of FIGS. 12A-B, the locking element 1224 is engaged after the sleeve 1222 is positioned over at least a portion of the socket 1228.

Turning to FIGS. 13A-B, an alternate embodiment of the fixation mechanism of FIGS. 12A-B is disclosed. FIGS. 13A-B, like FIGS. 12A-B, disclose a fixation mechanism in conjunction with an inferior implant 1204. The inferior implant 1204 and the securing mechanism 1220 are the same as shown in FIGS. 12A-B. In FIGS. 13A-B, however, the sleeve 1322 and the locking element 1324 are integrally formed. Stated another way, locking mechanism is a sleeve 1322 that includes a locking element 1324. Thus, tightening the locking element 1324 causes the sleeve 1322 to move into position over a portion of the socket 1228 as the locking element 1324 is tightened.

Like the sleeve 1222 the sleeve 1322 at least partially surrounds the shaft 1226 and is moveable with respect to the shaft 1226. Preferably, the sleeve 1322 is configured to be positioned over at least a portion of the socket 1228 such that the lateral expansion of the socket 1228 is limited by the sleeve 1322. In use, the sleeve 1322 is preferably positioned over at least a portion the socket 1228 following engagement of the socket 1228 and knob 1205 to prevent the knob 1205 and the socket 1228 from disengaging.

The sleeve 1322 preferably has threads 1334 on at least part of the internal surface of the sleeve 1322 for engagement with the threads 1230 of the shaft 1226. The sleeve 1322 is preferably only partially threaded such that the area to be positioned over the socket 1228 is not internally threaded.

Like the locking element 1224, the locking element 1324 may be configured to engage the side of the securing mechanism 1220 opposite the socket 1228 to limit movement of the fixation mechanism 1206 with respect to a bone. Preferably, the locking element 1324 is also a lagging element that lags the inferior implant 1204 as the locking element 1324 is engaged. The locking element 1324 also preferably has internal threads 1338 for engaging the external threads 1230 of the shaft 1226.

The fixation mechanisms 1206 and 1306 mechanism may be made from any material known in art for medical fixation devices. For example, the translaminar fixation mechanism may be made from titanium, titanium/aluminum/vanadium (Ti/Al/V) alloys, Tantalum, CrCo, ceramic, carbon or carbon composite materials. In addition, the fixation mechanisms may include surfaces (e.g., the outer surfaces of the sleeve 1222 or 1322, the outer surfaces of the locking elements 1224 or 1324 or the outer surfaces of the securing mechanism 1226) that are porous to facilitate cementless fixation to bone. For example, the surfaces may be beaded, threaded, textured, etc. Further, the surfaces may have hydroxyapatite coatings or may be plasma-sprayed. In addition to the examples listed, any known method of improving fixation of biologic implants may be used.

Figure 14:
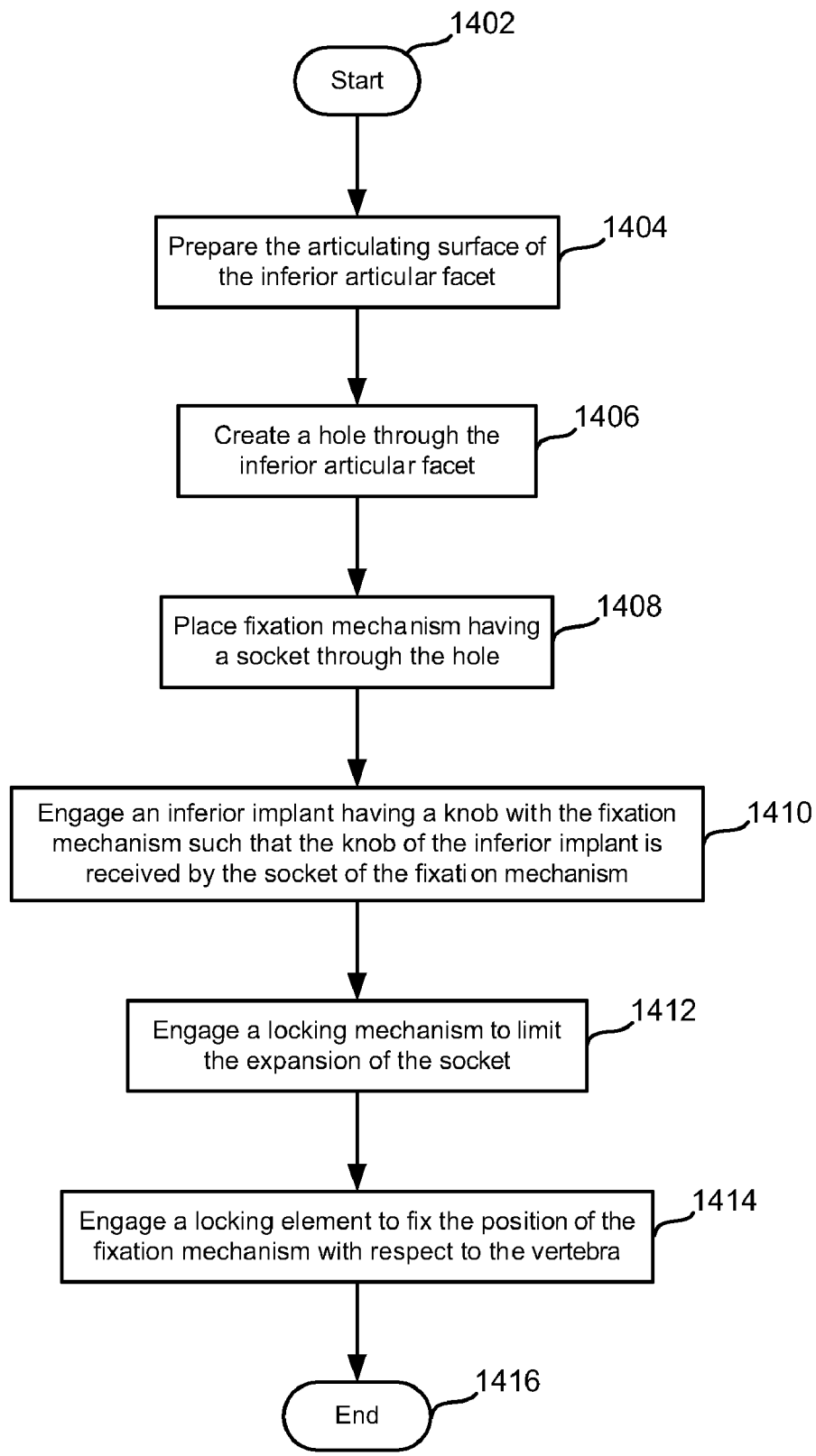
FIG. 14 is a flow chart generally illustrating a method for securing an implant having a knob to an inferior articular facet of a vertebra.

Turning next to FIG. 14, provided is a flow chart generally illustrating a method for securing an implant having a knob to an inferior articular facet of a vertebra. The overall flow begins at process block 1402, from which progression continues to process block 1404, wherein a space is created between the superior articular facet 30 and the inferior articular facet 32. It will be understood by those skilled in the art that prior to creating the space, it may be preferable or even necessary to expose the facet joint 36 at an effected level and remove the capsule. The effected level may be exposed through use of any appropriate procedure, such as a modified "Wiltse" approach. The creation of the space at process block 1404 may be accomplished by using a curette or similar device and by removing the cartilaginous surfaces of the facet joint 36. In one exemplary embodiment, the created space is sufficient for using a rasp on an articulating surface of an articular facet.

The space created between the superior articular facet 30 and the inferior articular facet 32 may range, for example, from about 2 mm to about 5 mm. In one exemplary embodiment, the space ranges from about 3 mm to about 4 mm. The creation of the space at process block 1404 may also include using at least one curette, at least one rasp, or at least one burr, such as a high speed burr, to resurface the bone prior to placement of the implants. In addition, the articulating surfaces may be prepared such that a bleeding bone bed is created to facilitate bone ingrowth for a superior implant and an inferior implant.

Flow progresses to process block 1406 wherein a hole is created through the inferior articular facet. Preferably, the hole created in process block 1406 extends through the inferior articular facet and traverses the connected lamina. Progression then continues to process block 1408 wherein a translaminar fixation mechanism is placed through the hole traversing the lamina and the inferior articular facet such that a socket at one end of the translaminar fixation mechanism is located at or near the space created at process block 1404.

Progression then continues to process block 1410 wherein the fixation mechanism and an inferior implant having a knob are engaged. More specifically, a knob extending from a fixation surface of the inferior implant is engaged with the socket of the fixation mechanism such that the knob is received by the socket. For example, the knob and the socket may be snapably engaged. Flow then continues to process block 1412 wherein a locking mechanism of the fixation mechanism is engaged to limit expansion of the socket. The engagement of the locking mechanism may involve, for example, causing a sleeve of the fixation mechanism to at least partially surround the socket. The sleeve may be caused to move toward the socket as a result of engaging the sleeve with a tool or driver configured to interact with a portion of the sleeve, or may be further caused by engaging a locking element integrally formed with the sleeve.

Progression then continues to process block 1414 wherein a locking element is engaged to fix the position of the fixation mechanism with respect to the vertebra. It will be understood that where the sleeve and locking element are integrally formed, for example, the engagement of the locking mechanism and the fixation of the position of the fixation mechanism may happen concurrently. The engagement of the locking mechanism may further involving lagging the inferior implant toward the inferior articular facet as the fixation mechanism is fixed.

Flow then continues to termination block 1416.

Figure 15:
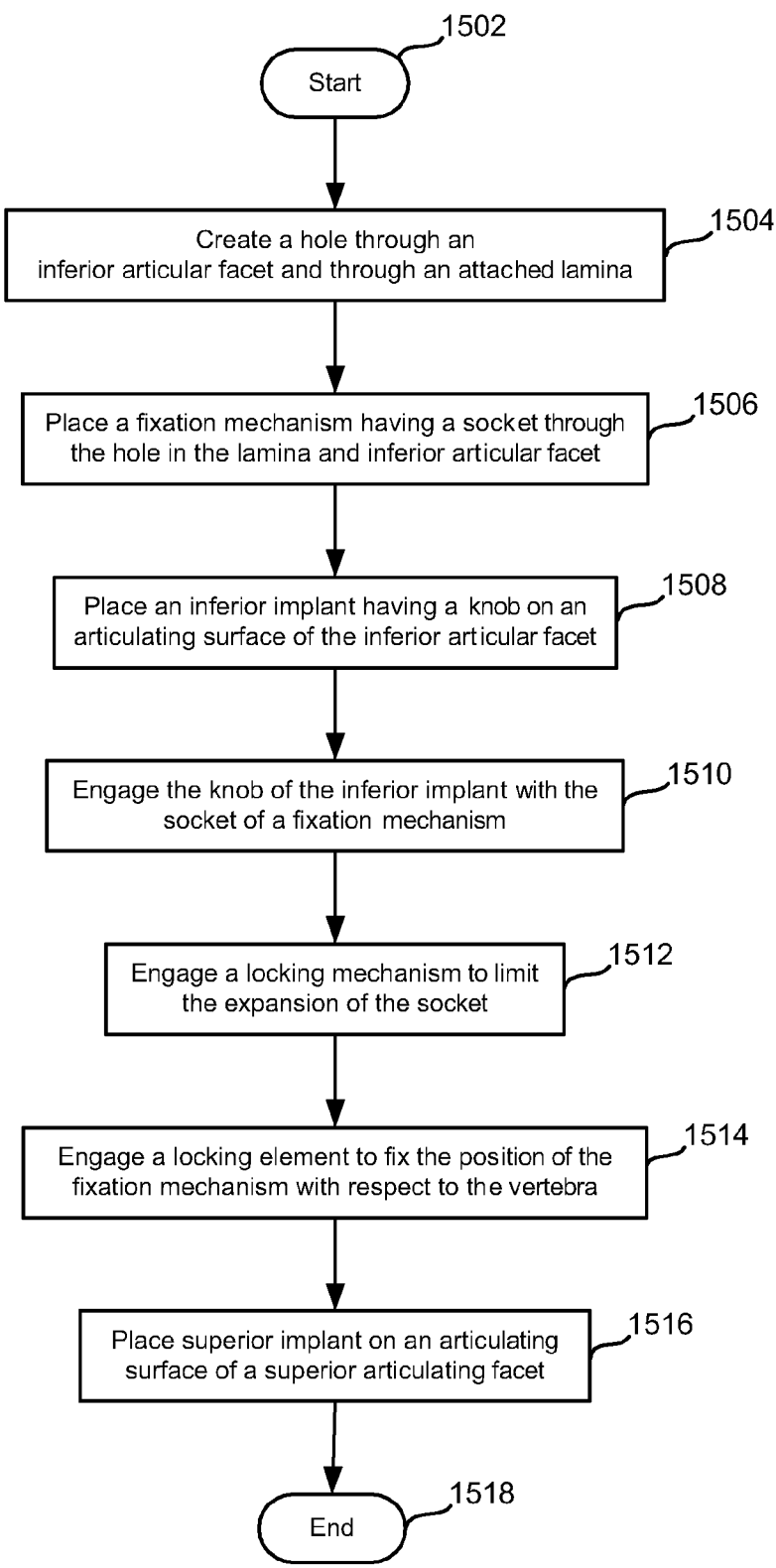
FIG. 15 is a flow chart generally illustrating a method for providing articulating surfaces for articular facets of a vertebra.

Turning next to FIG. 15, a flow chart generally illustrating a method for providing articulating surfaces for facet joint articular facets is provided. The overall flow begins at process block 1502, from which progression continues to process block 1504, wherein a hole is created through the inferior articular facet. Preferably, the hole created in process block 1504 extends through the inferior articular facet and traverses the connected lamina. Progression then continues to process block 1506 wherein a translaminar fixation mechanism is placed through the hole traversing the lamina and the inferior articular facet such that a socket at one end of the translaminar fixation mechanism is located at or near the inferior articular facet articulating surface.

Flow then continues to process block 1508 wherein an inferior articular facet having a knob extending from a fixation surface is placed on the articulating surface of the inferior articulating facet. Progression then flows to process block 1510 wherein the fixation mechanism and an inferior implant having a knob are engaged. More specifically, a knob extending from a fixation surface of the inferior implant is engaged with the socket of the fixation mechanism such that the knob is received by the socket. For example, the knob and the socket may be snapably engaged.

Flow then continues to process block 1512 wherein a locking mechanism of the fixation mechanism is engaged to limit expansion of the socket. The engagement of the locking mechanism may involve, for example, causing a sleeve of the fixation mechanism to at least partially surround the socket. The sleeve may be caused to move toward the socket as a result of engaging the sleeve with a tool or driver configured to interact with a portion of the sleeve, or may be further caused by engaging a locking element integrally formed with the sleeve.

Progression then continues to process block 1514 wherein a locking element is engaged to fix the position of the fixation mechanism with respect to the vertebra. It will be understood that where the sleeve and locking element are integrally formed, for example, the engagement of the locking mechanism and the fixation of the position of the fixation mechanism may happen concurrently. The engagement of the locking mechanism may further involve lagging the inferior implant toward the inferior articular facet as the fixation mechanism is fixed.

Flow then continues to process block 1516 wherein a superior implant is placed on an articulating surface of the superior articular facet adjacent the inferior articular facet upon which the inferior implant was placed. Flow then continues to termination block 1518.

While the present invention has been described in association with several exemplary embodiments, the described embodiments are to be considered in all respects as illustrative and not restrictive. Such other features, aspects, variations, modifications, and substitution of equivalents may be made without departing from the spirit and scope of this invention which is intended to be limited solely by the scope of the following claims. Also, it will be appreciated that features and parts illustrated in one embodiment may be used, or may be applicable, in the same or in a similar way in other embodiments. In addition, it will be understood that the fixation mechanisms disclosed herein may be used in other biologic environments other than those specifically set forth herein and are not limited to translaminar fixation mechanisms or to spinal implant fixation mechanisms.

While the present invention has been described in association with exemplary embodiments, the described embodiments are to be considered in all respects as illustrative and not restrictive. Such other features, aspects, variations, modifications, and substitution of equivalents may be made without departing from the spirit and scope of this invention, which is intended to be limited only by the scope of the following claims. Also, it will be appreciated that features and parts illustrated in one embodiment may be used, or may be applicable, in the same or in a similar way in other embodiments.

Although the invention has been shown and described with respect to certain embodiments, it is obvious that certain equivalents and modifications may be apparent to those skilled in the art upon the reading and understanding of the specification. The present invention includes all such equivalents and modifications, and is limited only by the scope of the following claims.

What is claimed is:

1. A fixation mechanism for fixing an orthopedic implant comprising:
   a securing mechanism having a shaft and a socket, the socket being configured to engage a knob of the orthopedic implant;
   a sleeve at least partially surrounding the shaft, wherein the sleeve is configured to be positioned over at least a portion of the socket such that lateral expansion of the socket is limited by the sleeve;
   a locking element configured to engage the side of the securing mechanism opposite the socket to limit movement of the fixation mechanism with respect to a bone;
   wherein the shaft comprises external threads and at least one of the sleeve or the locking element comprises internal threads; and
   wherein the fixation mechanism is an orthopedic implant adapted for permanent implantation.

2. The fixation mechanism of claim 1 wherein the socket and the knob of the orthopedic implant are snapably engageable.

3. The fixation mechanism of claim 1 wherein the socket comprises slots to facilitate expansion.

4. The fixation mechanism of claim 1 wherein the locking element and the sleeve are integrally formed.

5. A facet implant comprising:
   an inferior implant configured for placement on an inferior articular facet of a vertebra, the inferior implant having a knob; and
   a fixation mechanism for securing the inferior implant to the inferior articular facet, the fixation mechanism comprising:
   a shaft,
   a socket configured to receive the knob of the inferior implant, and
   a locking mechanism for limiting expansion of the socket following receipt of the knob of the inferior implant;
   wherein the shaft comprises external threads and the locking mechanism comprises internal threads.

6. The facet implant of claim 5 wherein the locking mechanism comprises a sleeve.

7. The facet implant of claim 6 wherein the sleeve comprises a locking element.

8. The facet implant of claim 5 wherein the fixation mechanism is capable of traversing a lamina connected to the inferior articular facet of the vertebra while engaging the knob of the inferior implant at or near the surface of an inferior articular facet of the vertebra.

9. A facet implant comprising:
   a superior implant configured for placement on a superior articular facet, the superior implant having an articulating surface and a fixation surface;
   an inferior implant configured for placement on an inferior articulating facet, the inferior implant having an articulating surface, a fixation surface, and a knob extending from the fixation surface; and
   a fixation mechanism for securing the inferior implant to the inferior articular facet, the fixation mechanism comprising a socket configured to receive the knob of the inferior implant, a shaft having external threads, and a locking element having internal threads.

10. The facet implant of claim 9 wherein the fixation mechanism further comprises a locking mechanism for limiting expansion of the socket following receipt of the knob of the inferior implant.

11. The facet implant of claim 10 wherein the locking mechanism comprises a sleeve and a locking element.

12. The facet implant of claim 9 wherein the socket comprises slots to facilitate expansion.

13. A method for securing an implant having a knob to an inferior articular facet of a vertebra comprising:
   creating a hole through the inferior articular facet;
   placing through the hole a fixation mechanism having a shaft with external threads, a locking mechanism with internal threads and a socket for receiving the knob of the implant;
   engaging the implant and the fixation mechanism such that the knob of the implant is received by the socket; and
   engaging the locking mechanism and the shaft to limit expansion of the socket following receipt of the knob of the implant.

14. The method of claim 13 wherein the hole passes through a lamina of the vertebra and the fixation mechanism traverses the lamina.

15. The method of claim 13 further comprising using at least one curette, at least one rasp, or at least one high speed burr to prepare the inferior articular facet prior to engaging the implant and the fixation mechanism.

16. The method of claim 13 wherein the fixation mechanism comprises a sleeve.

17. The method of claim 16 further comprising engaging a locking element to fix the position of the fixation mechanism with respect to the vertebra.

18. The method of claim 13 wherein the knob and the socket are snapably engaged.

19. A method for providing articulating surfaces for facet joint articular facets comprising:
   placing an inferior implant having a knob on an articulating surface of an inferior articular facet;

engaging the knob of the inferior implant with a socket of a fixation mechanism having a shaft with external threads and a locking mechanism with internal threads;

engaging the locking mechanism and the shaft to limit expansion of the socket following receipt of the knob of the inferior implant; and placing a superior implant on an articulating surface of a superior articular facet such that an articulating surface of the superior implant is capable of articulating with an articulating surface of the inferior implant.

20. The method of claim 19 further comprising creating a hole through the inferior articular facet.

21. The method of claim 20 wherein the hole passes through a lamina attached to the inferior articular facet.

22. The method of claim 21 further comprising placing the fixation mechanism through the hole such that the fixation mechanism traverses the lamina.

* * * * *